(12) United States Patent
Pamukcu et al.

(10) Patent No.: US 6,380,206 B1
(45) Date of Patent: Apr. 30, 2002

(54) METHOD OF INHIBITING NEOPLASTIC CELLS WITH 4,5-DIAMINOPYRIMIDINE DERIVATIVES

(75) Inventors: Rifat Pamukcu, Spring House; Gary Piazza, Doylestown, both of PA (US)

(73) Assignee: Cell Pathways, Inc., Horsham, PA (US)

( * ) Notice: Subject to any disclaimer, the term of this patent is extended or adjusted under 35 U.S.C. 154(b) by 0 days.

(21) Appl. No.: 09/850,510

(22) Filed: May 7, 2001

Related U.S. Application Data

(63) Continuation of application No. 09/199,081, filed on Nov. 23, 1998, now abandoned.

(51) Int. Cl.[7] ............................................. A61K 31/505
(52) U.S. Cl. ...................................................... 514/269
(58) Field of Search ......................................... 514/269

*Primary Examiner*—Dwayne C. Jones
(74) *Attorney, Agent, or Firm*—Robert W. Stevenson

(57) ABSTRACT

A method for inhibiting neoplasia, particularly cancerous and precancerous lesions by exposing the affected cells to 4,5-diaminopyrimidine derivatives.

6 Claims, No Drawings

METHOD OF INHIBITING NEOPLASTIC CELLS WITH 4,5-DIAMINOPYRIMIDINE DERIVATIVES

This application is a Continuation of prior U.S. Application Ser. No. 09/199,081 filed Nov. 23, 1998, abandoned on May 8, entitled "Method of Inhbiting Neoplastic Cells with 4,5-Diaminopyrimidene Derivatives," which is incorporated herein by reference.

TECHNICAL FIELD

This invention relates to a method for the inhibition of neoplastic cells, for example, for the treatment or prevention of precancerous lesions or other neoplasias in mammals.

BACKGROUND OF THE INVENTION

Each year in the United States alone, untold numbers of people develop precancerous lesions, which is a form of neoplasia, as discussed below. Such lesions exhibit a strong tendency to develop into malignant tumors, or cancer. Such lesions include lesions of the breast (that can develop into breast cancer), lesions of the skin (that can develop into malignant melanoma or basal cell carcinoma), colonic adenomatous polyps (that can develop into colon cancer), and other such neoplasms. Compounds that prevent or induce the remission of existing precancerous or cancerous lesions or carcinomas would greatly reduce illness and death from cancer.

For example, approximately 60,000 people die from colon cancer, and over 150,000 new cases of colon cancer are diagnosed each year. For the American population as a whole, individuals have a six percent lifetime risk of developing colon cancer, making it the second most prevalent form of cancer in the country. Colon cancer is also prevalent in Western Europe. It is believed that increased dietary fat consumption is increasing the risk of colon cancer in Japan.

In addition, the incidence of colon cancer reportedly increases with age, particularly after the age of 40. Since the mean ages of populations in America and Western Europe are increasing, the prevalence of colorectal cancer should increase in the future.

To date, little progress has been made in the prevention and treatment of colorectal cancer, as reflected by the lack of change in the five-year survival rate over the last few decades. The only cure for this cancer is surgery at an extremely early stage. Unfortunately, most of these cancers are discovered too late for surgical cure. In many cases, the patient does not experience symptoms until the cancer has progressed to a malignant stage.

In view of these grim statistics, efforts in recent years have concentrated on colon cancer prevention. Colon cancer usually arises from pre-existing benign neoplastic growths known as polyps. Prevention efforts have emphasized the identification and removal of colonic polyps. Polyps are identified by x-ray and/or colonoscopy, and usually removed by devices associated with the colonoscope. The increased use of colon x-rays and colonoscopies in recent years has detected clinically significant precancerous polyps in four to six times the number of individuals per year that acquire colon cancer. During the past five years alone, an estimated 3.5 to 5.5 million people in the United States have been diagnosed with adenomatous colonic polyps, and it is estimated that many more people have or are susceptible to developing this condition, but are as yet undiagnosed. In fact, there are estimates that 10–12 percent of people over the age of 40 will form clinically significant adenomatous polyps.

Removal of polyps has been accomplished either with surgery or fiber-optic endoscopic polypectomy—procedures that are uncomfortable, costly (the cost of a single polypectomy ranges between $1,000 and $1,500 for endoscopic treatment and more for surgery), and involve a small but significant risk of colon perforation. Overall, about $2.5 billion is spent annually in the United States in colon cancer treatment and prevention.

In the breast, breast cancer is often treated surgically, often by radical mastectomy with its painful aftermath. Such surgery is costly, too.

As indicated above, each lesion carries with it a chance that it will develop into a cancer. The likelihood of cancer is diminished if a precancerous lesion is removed. However, many of these patients demonstrate a propensity for developing additional lesions in the future. They must, therefore, be monitored periodically for the rest of their lives for reoccurrence.

In most cases (i.e. the cases of sporadic lesion formation, e.g. so-called common sporadic polyps), lesion removal will be effective to reduce the risk of cancer. In a small percentage of cases (i.e. cases where numerous lesions form, e.g. the so-called polyposis syndromes), removal of all or part of the effected area (e.g. the colon) is indicated. For example, the difference between common sporadic polyps and polyposis syndromes is dramatic. Common sporadic polyp cases are characterized by relatively few polyps which can usually be removed leaving the colon intact. By contrast, polyposis syndrome cases can be characterized by many (e.g. hundreds or more) of polyps—literally covering the colon in some cases—making safe removal of the polyps impossible short of surgical removal of the colon.

Because each lesion carries with it a palpable risk of cancerous development, patients who form many lesions (e.g. polyposis syndrome patients) invariably develop cancer if left untreated. Surgical removal of the colon is the conventional treatment in polyposis patients. Many polyposis patients have undergone a severe change in lifestyle as a result of the disfiguring surgery. Patients have strict dietary restrictions, and many must wear ostomy appliances to collect their intestinal wastes.

The search for drugs useful for treating and preventing cancer is intensive. Indeed, much of the focus of cancer research today is on the prevention of cancer because chemotherapy for cancer itself is often not effective and has severe side effects. Cancer chemoprevention is important for recovered cancer patients who retain a risk of cancer reoccurrence. Also, cancer prevention is important for people who have not yet had cancer, but have hereditary factors that place them at risk of developing cancer. With the development of new genetic screening technologies, it is easier to identify those patients with high-risk genetic factors, such as the potential for polyposis syndrome, who would greatly benefit from chemopreventative drugs. Therefore, finding such anti-cancer drugs that can be used for prolonged preventive use is of vital interest.

Known chemopreventative and chemotherapeutic drugs are believed to kill cancer cells by inducing apoptosis, sometimes referred to as "programmed cell death." Apoptosis naturally occurs in virtually all tissues of the body, and especially in self-renewing tissues such as bone marrow, immune cells, gut, liver and skin. Apoptosis plays a critical role in tissue homeostasis, that is, it ensures that the number of new cells produced are correspondingly offset by an equal number of cells that die. For example, the cells in the intestinal lining divide so rapidly that the body must eliminate cells after only three days in order to prevent the overgrowth of the intestinal lining.

Recently, scientists have realized that abnormalities of apoptosis can lead to the formation of precancerous lesions and carcinomas. Also, recent research indicates that defects in apoptosis play a major role in other diseases in addition to cancer. Consequently, compounds that modulate apoptosis could be used to prevent or control cancer, as well as used in the treatment of other diseases.

Unfortunately, even though known chemotherapeutic drugs may exhibit such desirable apoptosis effects, most chemotherapeutic drugs have serious side effects that prohibit their long-term use, or use in otherwise healthy individuals with precancerous lesions. These side effects, which are a result of the high levels of cytotoxicity of the drugs, include hair loss, weight loss, vomiting, immune suppression and other toxicities. Therefore, there is a need to identify new drug candidates for therapy that do not have such serious side effects in humans.

In recent years, several non-steroidal anti-inflammatory drugs ("NSAIDs"), originally developed to treat arthritis, have shown effectiveness in inhibiting and eliminating colonic polyps. Polyps virtually disappear when the patients take the drug, particularly when the NSAID sulindac is administered. However, the prophylactic use of currently available NSAIDs, even in polyposis syndrome patients, is marked by severe side reactions that include gastrointestinal irritations, perforations, ulcerations and kidney toxicity. Once NSAID treatment is terminated due to such complications, the polyps return, particularly in polyposis syndrome patients.

Sulindac has been particularly well received among the NSAIDs for polyp treatment. Sulindac is a sulfoxide compound that itself is believed to be inactive as an anti-arthritic agent. The sulfoxide is reportedly converted by liver enzymes to the corresponding sulfide, which is acknowledged to be the active moiety as a prostaglandin synthesis inhibitor. The sulfide, however, is associated with the side effects of conventional NSAIDs. The sulfoxide is also known to be metabolized to a sulfone compound that has been found to be inactive as an inhibitor of prostaglandin synthesis but active as an inhibitor of precancerous lesions.

SUMMARY OF THE INVENTION

This invention includes a method of inhibiting neoplastic cells by exposing those cells to a pharmacologically effective amount of those compounds described below. Such compounds are effective in modulating apoptosis and eliminating and inhibiting the growth of neoplasias such as precancerous lesions, but are not characterized by the severe side reactions of conventional NSAIDs or other chemotherapeutics.

The compounds of that are useful in the methods of this invention include those of Formula I:

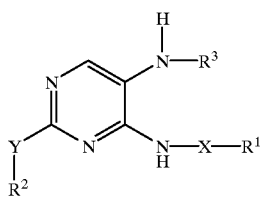

wherein
X is selected from the group consisting of a direct bond, $C_{1-4}$ alkylene, $C_{1-4}$ alkyleneoxy, $C_{1-4}$ alkoxyphenyl or phenyl $C_{1-4}$ alkylene;

Y is selected from the group consisting of a direct bond or $C_{1-2}$ alkyl;

$R^1$ is selected from the group consisting of (i) 5–15 membered cyclic or branched chain heterocompound which includes one or two selected from a group consisting of nitrogen, oxygen and sulfur and which is substituted with one or two selected from a group consisting of hydrogen, halogen, nitro, hydroxy, $C_{1-6}$ alkyl, $C_{3-6}$ alkenyl and halogen $C_{1-4}$ alkoxy, (ii) $C_{4-10}$ carbocyclic compound or (iii) hydroxy $C_{1-4}$ alkoxy;

$R^2$ is selected from the group consisting of 5–15 membered cyclic or branched chain heterocompound which includes one or two selected from a group consisting of nitrogen, oxygen and sulfur and which is substituted with one or two selected from a group consisting of hydrogen, hydroxy, halogen, nitro, hydroxy $C_{1-5}$ alkyl $C_{1-6}$ alkyl, $C_{3-6}$ alkenyl, and halogen $C_{1-4}$ alkoxy;

$R^3$ is selected from the group consisting of hydrogen, —C(O)$R^4$, or —S(O)$_2R^5$;

$R^4$ and $R^5$ are each independently selected from the group consisting of hydroxy, $C_{1-6}$ alkyl, $C_{3-7}$ cycloalkyl, $C_{3-6}$ alkenyl, halogen $C_{1-6}$ alkyl, halogen, $C_{2-6}$ alkenyl and $C_{1-4}$ alkoxy; or $R_4$ and $R_5$ represent each independently

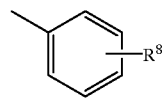

and $R_6$ is selected from a group consisting of hydrogen, hydroxy, $C_{1-6}$ alkyl, $C_{3-6}$ alkenyl, halogen, $C_{1-6}$ alkyl, halogen, nitro and $C_{1-4}$ alkoxy.

The compounds of formula I may have optical isomers or geometrical isomers. These isomers are included in practice of the methods of the present invention.

DETAILED DESCRIPTION OF THE PREFERRED EMBODIMENTS

As indicated above, this invention relates to a method for inhibiting neoplasia, particularly cancerous and precancerous lesions by exposing the affected cells to a compound of Formula I above.

Preferably, such compounds are administered without therapeutic amounts of an NSAID.

The present invention is also a method of treating mammals with precancerous lesions by administering a pharmacologically effective amount of an enterically coated pharmaceutical composition that includes compounds of this invention.

Also, the present invention is a method of inhibiting the growth of neoplastic cells by exposing the cells to an effective amount of compounds of Formula I, wherein $R_1$ through $R_3$ are defined as above.

In still another form, the invention is a method of inducing apoptosis in human cells by exposing those cells to an effective amount of compounds of Formula I to those cells sensitive to such a compound.

As used herein, the term "precancerous lesion" includes syndromes represented by abnormal neoplastic, including dysplastic, changes of tissue.

Examples include adenomatous growths in colonic, breast or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), prostatic dysplasia, bronchial dysplasia, breast, bladder and/or skin and related conditions (e.g., actinic keratosis), whether the lesions are clinically identifiable or not.

As used herein, the term "carcinomas" refers to lesions that are cancerous. Examples include malignant melanomas, breast cancer, and colon cancer.

As used herein, the term "neoplasm" refers to both precancerous and cancerous lesions.

It will also be appreciated that a compound of Formula I or a physiologically acceptable salt or solvate thereof can be administered as the raw compound, or as a pharmaceutical composition containing either entity.

Compounds useful in the methods of this invention are preferably formulated into compositions together with pharmaceutically acceptable carriers for oral administration in solid or liquid form, or for rectal administration, although carriers for oral administration are most preferred.

Pharmaceutically acceptable carriers for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers include liquid dosage forms for oral administration, e.g. pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers for rectal administration are preferably suppositories that may contain, in addition to the compounds of Formula I, excipients such as cocoa butter or a suppository wax.

The pharmaceutically acceptable carrier and compounds of this invention are formulated into unit dosage forms for administration to a patient. The dosage levels of active ingredient (i.e. compounds of this invention) in the unit dosage may be varied so as to obtain an amount of active ingredient effective to achieve lesion-eliminating activity in accordance with the desired method of administration (i.e., oral or rectal). The selected dosage level therefore depends upon the nature of the active compound administered, the route of administration, the desired duration of treatment, and other factors. If desired, the unit dosage may be such that the daily requirement for active compound is in one dose, or divided among multiple doses for administration, e.g., two to four times per day.

The pharmaceutical compositions of this invention are preferably packaged in a container (e.g. a box or bottle, or both) with suitable printed material (e.g. a package insert) containing indications, directions for use, etc.

For administration to humans in the curative or prophylactic treatment of the disorders identified above, oral dosages of a compound of Formula I will generally be in the range of from 0.5–800 mg daily for an average adult patient (70 kg). Thus for a typical adult patient, individual tablets or capsules contain from 0.2–400 mg of active compound, in a suitable pharmaceutically acceptable vehicle or carrier, for administration in single or multiple doses, once or several times per day. Dosages for intravenous, buccal or sublingual administration will typically be within the range of from 0.1–400 mg per single dose as required. In practice, the physician will determine the actual dosing regimen that will be most suitable for an individual patient and it will vary with the age, weight and response of the particular patient.

A process for producing compounds of formula I comprises (a) reacting a compound of formula III:

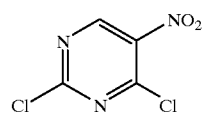

with a compound of formula III-a:

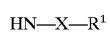

which X and $R^1$ represent the same as defined above, to give a compound of formula IV:

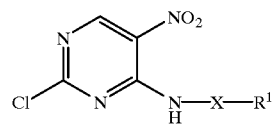

which X and $R^1$ represent the same as defined above, (b) reacting the compound IV with a compound of the general formula IV-a: $Y-R^2$ in which Y and $R^2$ represent the same as defined above, to give a compound of the general formula V:

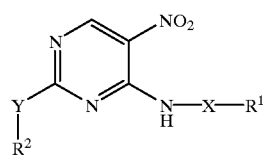

in which X, $R^1$ and $R^2$ represent the same as defined above, (c) reducing the compound V to give a compound of the general formula VI:

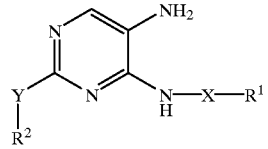

in which X, Y, $R^1$ and $R^2$ represent the same as defined above, (d–i) reacting the compound VI with a compound of (VI-I):

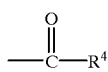

in which $R^4$ is selected from a group consisting of hydroxy, $C_{1-6}$ alkyl, $C_{3-7}$ cycloalkyl, $C_{3-6}$ alkenyl, halogen $C_{1-6}$ alkyl, halogen $C_{2-6}$ alkenyl and $C_{1-4}$ alkoxy or $R^4$ represents

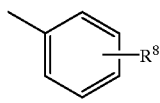

in which $R^6$ is selected from the group consisting of hydrogen, hydroxy, $C_{1-6}$ alkyl, $C_{3-6}$ alkenyl, halogen $C_{1-6}$ alkyl, halogen, nitro, and $C_{1-4}$ alkoxy to give a compound of formula I-B:

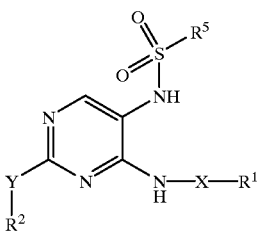

in which x, Y, $R^1$, $R^2$ and $R^5$ are the same as defined above.

The compound III is reportedly described in WO 9510506 and, reportedly, can be prepared by reacting the compound 11 with phosphorus oxychloride in the presence of a base. N,N-diethyl-aniline, N,N-dimethylaniline or NN-diisopropylethylamine can be used as the base. As such, the reaction is carried out at a reflux temperature.

The compound IV can be prepared by reacting the compound III with the compound of formula III-a: HN—X—$R^1$ in which $R^1$ is the same as defined above, preferably, using pyridine or triethylamine in solvent such as dichloromethane or acetonitrile at 0° C. to room temperature (J. Med. Chem. 1994, 37, 2106).

The compound V can be prepared by dissolving the compound IV in a polar solvent and reacting the solution with the compound of the formula IV-a: Y—$R^2$ in which $R^2$ is the same as defined above, at 0° C. to reflux temperature. Usually, the compound V is obtained as crystals in acetonitrile, ethanol or isopropanol.

The compound VI is obtained by reacting the compound V with iron and acid in polar solvent under reflux (see, e.g., WO 9518097) or by reacting the compound V with sodium borohydride and 5% palladium on activated carbon in solvent such as methanol or ethanol at 0° C. to 25° C. (*Synthesis*, 1994, 1437).

The compound 1-A is produced by reacting the compound VI with the compound VI-a: —C(O)$R^4$ in which $R^4$ is the same as defined above, using pyridine, triethylamine or N,N-diisopropyl ethyl amine as a base in solvent such as acetonitrile, dichloromethane or tetrahydrofurane at 0° C. to reflux temperature.

The compound 1-B is produced by reacting compound VI with the compound VI-b: —S(O)$_2$$R^5$ in which $R^5$ is as defined above, using pyridine or N,N-diisopropylethylamine as a base in solvent such as acetonitrile, dichloromethane or tetrahydrofurane at 0° C. to 25° C.

The invention will now be described with reference to the following illustrative Examples from PCT KR 00155, which is incorporated herein by reference.

REFERENCE EXAMPLE 1

2,4-Dichloro-5-nitropyrimidine 25 g of 5-nitrourasil is suspended in 490 ml of phosphorous oxychloride for 10 minutes and diisopropylethylamine is slowly added to the suspension at room temperature. The reaction suspension is refluxed at 130° C. for 3 hours. The solution is concentrated under reduced pressure to be a volume of 100 ml, Then., the solution is added dropwise to 500 ml of ice water and stirred for 1 hour, and extracted with diethyl ether (300 ml×5). The organic layer is washed with 500 ml of saturated ammonium chloride and dried over anhydrous magnesium sulfate and concentrated under reduced pressure. Column chromatography on silica gel (ethyl acetate hexane;=1:5) affords 16.8 g of the title compound.

NMR (CDCl$_3$, 400 MHz): δ=8.82(IH, s).

REFERENCE EXAMPLE 2

4N-Benzyl-2-chloro-5-nitropyrimidineamine 2.7 ml of benzylamine is added to a solution of 5.0 g of the 2,4-dichloro-5-nitropyrimidine (Reference Example 1) in 75 ml of dichloromethane at 5° C., and the solution is stirred for 1 hour. 3.6 ml of triethylamine is added to the solution at 5t, stirred for 10 minutes, washed with 150 ml of saturated sodium bicarbonate, dried over anhydrous magnesium sulfate, and concentrated under reduced pressure to obtain 6.6 g of the title compound.

NMR(CDCl$_3$, 400 MHz): δ=4.68(2H, d), 7.17(5H, m), 8.65(1H, t), 8.84(1H, s).

REFERENCE EXAMPLE 3

4N-(4-Bromobenzyl)-2-chloro-5-nitroiyrimidineamine 2,4-dichloro-5-nitropyrimidine obtained by Reference Example 1 is used as a starting material and is reacted in the same manner as Reference Example 2 to obtain the title compound.

NMR (CDCl$_3$, 400 MHz): δ=4.81(2H, d), 7.32(2H, d), 7.45(2H, d), 8.61(1H, t), 8.95(1H, s).

REFERENCE EXAMPLE 4

2-Chloro-4N-(2-chlorobenzyl)-5-nitropyrimidineamine 2,4-dichloro-5-nitropyrimidine obtained by Reference Example 1 is used as a starting material and is reacted in the same manner as Reference Example 2 to obtain the title compound.

NMR (CDCl$_3$, 400 MHz): δ=4.75(2H, d), 7.43(3H, d), 7.48(1H, d), 8.61(1H, t), 8.85(1H, s).

REFERENCE EXAMPLE 5

2-Chloro-4N-(1,3-dioxaindan-5-yl)methyl-5-nitropyrimidineamine 3.0 ml of piperonylamine is added to a solution of 5.0 g of 2,4-dichloro-5-nitropyrimidine obtained by Reference Example 1 in 75 ml of dichloromethane at 5° C., and the solution is stirred for 1 hour. 3.6 ml of triethylamine is then added to the reaction solution at 5° C., stirred for 10 minutes, washed with saturated sodium bicarbonate, dried over anhydrous magnesium sulfate, and concentrated under reduced pressure to obtain 6.9 g of the title compound.

NMR(CDCl$_3$, 400 MHz): δ=4.60(2H, d), 5.95(2H, s), 6.86(1H, d), 6.91(1H, d), 7.03(1H, d), 8.61(1H, t), 8.85(1H, s).

REFERENCE EXAMPLE 6

Ethyl 1-(4-benzylamino-5-nitropyrimidine-2-yl)-4-piperidinecarboxylate 3.5 ml of isonipecotate is added to a solution of 1.0 g of 4N-benzyl-2-chloro-5-nitropyrimidineamine (Reference Example 2) in 35 ml of acetonitrile and the suspension is stirred overnight. 35 ml of ethanol is added to the suspension, cooled to 5° C. and stirred for 1 hour. Filtration afforded 0.91 g of the yellowish title compound.

NMR(CDCl$_3$, 400 MHz): δ=1.06(31-1, t), 1.51(211, m), 1.79(2H, ABq), 2.39(1H, m), 2.97(2H, m), 3.95(2H, q), 4.40(2H, d), 4.54(2H, d), 7.15(5H, m), 8.54(1H, t), 8.82(1H, s).

REFERENCE EXAMPLE 7

4N-Benzyl-2-(4-ethylpiperazino)-5-nitro-4-pyrimidineamine 4N-benzyl-2-chloro-5-nitropyrimidineamine (Reference Example 2) is used as a starting material and is reacted in the same manner as Reference Example 6 to obtain the title compound.

NMR(CDCl$_3$, 400 MHz): δ=0.93(3H, t), 2.25(6H, m), 3.79(4H, m), 4.55(2H, d), 7.16(SH, m), 8.58(IH, 8.81(1H, s)

REFERENCE EXAMPLE 8

4N-(4-Bromobenzyl)-2-(1H-imidazol-1-yl)-5-nitropyrimidineamine 4N-(4-bromobenzyl)-2-chloro-5-nitropyrimidineamine (Reference Example 3) is used as a starting material and is reacted in the same manner as Reference Example 6 to obtain the title compound. NMR(DMSO-d$_6$, 400 MHz): δ=4.81(2H, d), 7.07(1H, s), 7.32(2H, d), 7.45(2H, d), 7.79 (1H, t), 8.47(1H, s), 9.16(1H, s), 9.67(1H, t).

REFERENCE EXAMPLE 9

Ethyl 1-[4-(1,3-dioxaindan-5-yl)methylamino-5-nitropyrimidine-2-yl]-4-piperidinecarboxylate 3.0 ml of ethyl isonipecotate is added to a solution of 1.0 g of 2-chloro-4N-(1,3-dioxaindan-5-yl)methyl-5-nitropyrimidineamine (Reference Example 5) in 45 ml of acetonitrile at room temperature and the suspension was stirred overnight. 45 ml of ethanol is added to the suspension, cooled to 51 ° C., and stirred for 1 hour. Filtration afforded 1.0 g of the yellowish title compound.

NMR (CDCl$_3$, 400 MHz): δ=1.26(3K t), 1.71(2H, m), 1.97(2H, ABq), 2.58 (1H, m), 3.18(2H, m), 4.15(2H, q), 4.52(2H, m), 4.67(2H, d), 5.94(2H, s), 6.78(3H, m), 8.63 (1H, t), 8.98(1H, s).

REFERENCE EXAMPLE 10

4N-(1,3-Dioxaindan-5-yl)methyl-2-(2-ethyl-4-methyl-1H-imidazol-1-yl)-5-nitropyrimidineamine The compound prepared by Reference Example 5 is used as a starting material and is reacted in the same manner as Reference Example 9 to obtain the title compound.

NMR (CDCl$_3$ , 400 MHz): δ=1.31(3H, t), 2.24(31-1, s), 3.22(211, q), 4.78(2H, d), 6.00(2H, s), 6.94(3H, m), 7.58 (1H, s), 8.72(1H, t), 9.25(1H, s).

REFERENCE EXAMPLE 11

Ethyl 1-[4-(1,3-dioxaindan-5-yl)methylamino-5-nitropyrimidine-2-yl)-4-piperazine Carboxylate 2.5 ml of ethyl 1-piperazinecarboxylate is added to a solution of 1.75 g of 2-chloro-4N-(1,3-dioxaindan-5-yl) methyl-5-nitropyrimidineamine (Reference Example 5) in 60 ml of acetonitrile and the suspension is stirred overnight. 100 ml of ethanol is added to the suspension, cooled to 5° C., and stir-red for 1.5 hour. Filtration affords 2.1 g of the title compound.

NMR (CDCl$_3$, 400 MHz): δ=1.55(3H, t), 3.77(4H, d), 4.01(4H, d), 4.48(2H, d), 4.77(2H, d), 6.10(2H, s), 7.00(2H, d), 7.04(1H, s), 8.25(1H, t), 9.11(1H, s).

REFERENCE EXAMPLE 12

4N-(1,3-Dioxaindan-5-yl)methyl-2-(1H-imidazol-1-yl)-5-nitropyrimidineamine 2.3 g of 1H-imidazole is added to a solution of 1.75 g of 2-chloro-4N-(1,3-dioxaindan-5-yl)methyl-5-nitropyrimidineamine (Reference Example 5) in 60 ml of acetonitrile, and the suspension is stirred overnight. The suspension is concentrated under reduced pressure to obtain solid. The resulting solid is suspended in water:ethanol=40 ml:100 ml, filtered, and dried to obtain 1.55 g of the title compound.

NMR (CDCl$_3$, 400 MHz): δ=4.72(2H, d), 6.09(2H, s), 6.98(2H, d), 7.03(1H, s), 7.13(1H, s), 7.80(1H, s), 8.35(1H, t), 8.40(1H, s), 9.18(1H, s).

REFERENCE EXAMPLE 13

4N-Benzyl-5-nitro-2-(1H-tetrazol-1-yl) pyrimidineamine 4.0 g of 4N-benzyl-2-chloro-5-nitropyrimidineamine (Reference Example 2) is added to a solution of 3.0 g of 1H-tetrazol in 120 ml of acetonitrile. A mixture of 2.5 ml of triethylamine and 45 ml of acetonitrile is added dropwise to the solution. The reaction solution is stirred overnight and is concentrated under reduced pressure to obtain solid. The resulting solid is suspended in 3N sodium hydroxide solution for 1 hour, filtered and dried to obtain 3.80 g of the title compound.

NMR (CDCl$_3$, 400 MHz): δ=4.99(2H, d), 7.44(5H, m), 8.79(1H, t) 9.32(1H, s), 9.48(1H s).

REFERENCE EXAMPLE 14

Ethyl 1-(5-amino-4-benzylaminopyrimidin-2-yl)-4-piperidinecarboxylate 1.3 ml of acetic acid, 1.3 ml of distilled water and 1.40 g of iron are added to a suspension of 0.90 g of ethyl 1-(4-benzylamino-5-nitropyrimidine-2-yl)-4-piperidinecarboxylate (Reference Example 6) in 50 ml of ethanol, and the reaction solution is refluxed for 5 hours. The dark blue solution is filtered to remove the insoluble substance, and concentrated under reduced pressure to obtain the thin yellow oily product. The resulting product was dissolved in dichloromethane and washed with 10% sodium carbonate(50 ml×2). The organic layer is dried over anhydrous magnesium sulfate and concentrated under reduced pressure to obtain 0.57 g of the title compound as an oily product.

NMR (DMSO-d$_6$, 400 MHz): δ=1.04(3H, t), 1.45(2H, m), 1.76(2H, m), 2.41(1H, m), 2.91(2H, m), 3.93(2H, q), 4.40 (2H, d), 4.48(2H, d), 5.31(2H, s), 7.20(5H, m), 7.54(1H, t), 7.62(1H, s).

REFERENCE EXAMPLE 15

4N-Benzyl-2-(4-ethylpiperazino)-5-pyrimidinediamine 4N-benzyl-2-(4-ethylpiperazino)-5-nitro-4-pyrimidineamine (Reference Example 7) is used as a starting material and is reacted in the same manner as Reference Example 14 to obtain the title compound.

NMR (CDCl$_3$, 400 MHz): δ=0.92(3H, t), 2.23(6H, m), 3.75(4H, m), 4.48(2H, d), 5.31(2H, s), 7.15(5H, m), 7.38 (1H, t), 7.60(1H, s).

REFERENCE EXAMPLE 16

4N-(4-Bromobenzyl)-2-(1H-imidazol-1-yl)-5-pyrimidinediamine

The compound prepared by Reference Example 8 is used as a starting material and is reacted in the same manner as Reference Example 14 to obtain the title compound.

NMR (DMSO-d$_6$, 400 MHz): δ=4.65(2H, D), 5.40(2H, s), 7.07(1H, s), 7.28(2H, d), 7.33(1H, t), 7.43(2H, d), 7.58(1H, s), 7.62(1H, s), 8.47(1H, s).

REFERENCE EXAMPLE 17

Ethyl 1-[5-amino-4-(1,3-dioxaindan-5-yl)methylamino)pyrimidine-2-yl]-4-piperidinecarboxylate 5.0 ml of acetic acid, 4.1 ml of distilled water and 4.1 g of iron are added to a suspension of 2.00 g of the compound prepared by Reference Example 9 in 120 ml of ethanol, and the suspension is refluxed for 3 hours. The dark blue suspension is filtered to remove the insoluble substance, and concentrated under reduced pressure to obtain the thin yellowish oily product. The resulting product is dissolved in dichloromethane and washed with 10% sodium carbonate (100 ml×2). The organic layer is dried over anhydrous magnesium sulfate, and concentrated under reduced pressure to yield 1.21 g of the thin yellow title compound.

NMR (DMSO-d$_6$, 400 MHz): δ=1.23(3H, t), 1.69(2H, m), 1.95(2H, q), 2.56(1H, m), 3.17(2H, m), 4.12(2H, q), 4.50 (2H, m), 4.67(2H, d), 5.43(2H, s), 5.96(2H, m), 6.76(3H, m), 7.58(1H, t), 7.65(1H, s).

REFERENCE EXAMPLE 18

4N-(1,3-Dioxaindan-5-yl)methyl-2-(2-ethyl-4-methyl-1H-imidazol-1-yl)-5-pyrimidinediamine The compound prepared by Reference Example 10 is used as a starting material and is reacted in the same manner as Reference Example 14 to obtain the title compound.

NMR (DMSO-d$_6$ 400 MHz): δ=1.20(3H, t), 2.27(3H, s), 3.17(2H, q), 4.55(2H, d), 5.33(2H, 5.98(2H, s), 6.86(2H, q), 6.93(1H, s), 7.60(1H, s), 7.77(1H, s), 7.93(1H, t).

REFERENCE EXAMPLE 19

Ethyl 1-[5-amino-4-(1,3-dioxaindan-5-yl)methylaminopyrimidine-2-yl)]4-piperazinecarboxylate 10.0 ml of acetic acid, 5.0 ml of distilled water and 4.01 g of iron are added to a suspension of 3.00 g of the compound prepared by Reference Example 11 in 150 ml of ethanol, and the suspension is refluxed for 3 hours. The dark blue suspension is filtered to remove the insoluble substance, and concentrated under reduced pressure to obtain the thin yellow oily product. The resulting product is dissolved in dichloromethane and washed with 10% sodium carbonate (150 ml×2). The organic layer is dried over anhydrous magnesium sulfate, and concentrated under reduced pressure, Column chromatography on silica gel (methanol dichloromethane=1:10) affords 2.0 g of the title compound as a thin yellow solid.

NMR (DMSO-d$_6$, 400 MHz): δ=1.52(314, t), 3.75(4H, d), 4.00(4H, d), 4.46(2H, q), 4.70(2H, d), 5.38(2H, s), 6.08(2H, s), 6.97(2H, d), 7.02(1H, s), 7.45(1H, t), 7.65(2H, s).

REFERENCE EXAMPLE 20

4N-(1,3-Dioxaindan-5-yl)methyl-2-(1H-imidazol-1-yl)-5-pyrimidinediamine

The compound prepared by Reference Example 12 is used as a starting material and is reacted in the same manner as Reference Example 14 to obtain the title compound.

NMR (DMSO-d$_6$, 400 MHz): δ=4.68(2H, d), 5.38(2H, s), 6.05(2H, s), 6.97(2H, d), 7.02(1H, s), 7.13(1H, s), 7.46(1H, t), 7.67(1H, s), 7.80(1H, s), 8.37(1(H, s).

REFERENCE EXAMPLE 21

4N-Benzyl-2-(1H-tetrazol-1-yl)-5-pyrimidinediamine

The compound prepared by Reference Example 13 is used as a starting material and is reacted in the same manner as Reference Example 14 to obtain the title compound.

NMR (DMSO-d$_6$, 400 MHz): δ=4.72(2H, d), 5.36(2H, s), 7.28(1H, t), 7.34(2H, t), 7.43(2H, t), 7,63(1H, s), 7.65(1H, t), 9.94(1H, s).

EXAMPLE 1

1-[4-Benzylamino5-(2-bromophenylsulfonamido)pyrimidin-2-yl)]4-piperidine-carboxylic Acid 230 mg of 2-bromobenzenesulfonyl chloride is added to a solution of 400 mg of the compound prepared by Reference Example 14 in 40 ml of ethanol at room temperature, and the solution is stirred for 10 minutes. 0.27 ml of pyridine is added to the yellow reaction solution, stirred at room temperature overnight, and concentrated under reduced pressure to remove the solvent. The oily product obtained therefrom is mixed with 50 ml of dichloromethane and washed with saturated sodium carbonate. The organic layer is dried over anhydrous magnesium sulfate and concentrated under reduced pressure. Column chromatography on silica gel (ethyl acetate hexane=1:1) affords 170 mg of the pink solid ester compound.

150 mg of the ester compound is dissolved in 30 ml of methanol. 15 ml of 1.5N sodium hydroxide is added to the solution and stirred for 30 minutes at room temperature. The reaction solution is concentrated under reduced pressure to remove the organic solvent. Then, the aqueous layer is adjusted to pH 4.0 by using 3.0 N hydrochloric acid and stirred for 30 minutes. Filtration affords 110 mg of the title compound as a white solid. m.p. 114–117° C.

NMR (DMSO-d$_6$, 400 MHz): δ=1.28(2H, m), 1.71(211, m), 2.40(1H, m), 2.81(2H, t), 4.30(2H, d), 4.46(2H, d), 7.01(1H, s), 7.21(1H, m), 7.27(5H, m), 7.52(2H, m,), 7.89 (2H, m,), 9.40(1H, s), 12.35(1H, s).

EXAMPLE 2

1-[4-Benzylamino-5-(4-bromophenylsulfonamido)pyrimidin-2-yl)]-4-piperidine-carboxylic Acid 210 mg of 4-bromobenzenesulfonyl chloride is added to a solution of 300 mg of the compound prepared by the Reference Example 14 in 40 ml of dichloromethane at room temperature, and the solution is stirred for 10 minutes 0.20 ml of pyridine is added to the yellow reaction solution, stirred for 30 hours at room temperature, washed with 50 ml of saturated sodium carbonate, and the organic layer is dried over anhydrous magnesium sulfate and concentrated under reduced pressure. The oily resulting material is purified by column chromatography on silica gel (methanol:dichloromethane=7.5% v/v) to obtain 300 mg of the yellow solid ester compound.

250 mg of the ester compound is dissolved in 30 mg of ethanol. 15 ml of 1.5N sodium hydroxide is added to the solution and stirred for 3.5 hours at room temperature. The reaction solution is concentrated under reduced pressure to remove the organic solvent. Then, the aqueous layer is adjusted to pH 4.0 by using 3.0 N hydrochloric acid and stirred for 1 hour at 5° C. Filtration affords 110 mg of the title compound as a white solid. m.p. 136–138° C.

NMR (DMSO-$d_6$, 400 MHz): δ=1.36(2H, m), 1.76(2H, m), 2.45(1H, m), 2.91(2H, t), 4.25(2H, d), 4.40(2H, d), 7.11(1H, s), 7.23(5H, m), 7.53(1H, s), 7.70(2H, d), 7.80(2H, d), 9.58(1H, s), 12.48(1H, brs).

EXAMPLE 3

1-[4-Benzylamino-5-(4-methylphenylsulfoneamido) pyrimidin-2-yl)]-4-piperidine-carboxylic Acid 180 mg of p-toluenesulfonyl chloride is added to a solution of 280 mg of the compound prepared by the Reference Example 14 in 40 ml of dichloromethane at room temperature, and the solution is stirred for 10 minutes. 0.20 ml of pyridine is added to the yellow reaction solution, and stirred for 14 hours at room temperature. The solution is washed with 30 ml of 1.5 N sodium hydroxide, the organic layer is dried over anhydrous magnesium sulfate and concentrated under reduced pressure to obtain 450 mg of the yellow solid ester compound.

450 mg of the ester compound. is dissolved in 50 mg of ethanol. 25 ml of 1.5 N sodium hydroxide is added to the solution and stirred for 2.5 hours at room temperature to complete the hydrolysis reaction. The reaction solution is concentrated under reduced pressure to remove the organic solvent. The aqueous layer is adjusted to pH 3.5 by using 3.0 N hydrochloric acid and stirred for 1 hour at 5° C. Filtration affords 170 mg of the title compound as a white solid. m.p. 126–127° C.

NMR (DMSO-$d_6$, 400 MHz): δ=1.31(2H, m), 1.72(2H, m), 2.39(3H, s), 2.41(1H, m), 2.82(2H, 1), 4.31(2H, d), 4.40(2H, d), 7.02(1H, s), 7.10(1H, t), 7.28(5H, m), 7.38(2H, d), 7.63(2H, d), 9.04(1H, s), 12.20(1H, s).

EXAMPLE 4

1-[4-Benzylamino-5-(4-chlorophenylcarboxamido) pyrimidin-2-y]-4-piperidine-carboxylic Acid The compound prepared by Reference Example 14 and 4-chlorobenzoyl chloride are used as starting materials and are reacted in the same manner as in Example 3 to obtain the title compound. m.p. 155–157° C.

NMR (DMSO-$d_6$, 400 MHz): δ=1.48(2H, m), 1.85(2H, m), 2.56(1H, m), 3.14(2H, t), 4.29(2H, d), 4.58(2H, d), 7.23(1H, t), 7.35(5H, m), 7.50(2H, d), 7.80(1H, s), 8.06(2H, d), 9.99(1H, s), 12.39(1H, s).

EXAMPLE 5

1-(4-Benzylamino-5-hexylcarboxamidopyrimidin-2-yl)-4-piperidinecarboxylic Acid

The compound prepared by Reference Example 14 and hexanoyl chloride are used as starting materials and are reacted in the same manner as Example 3 to obtain the title compound. m.p. 245° C. (decomposition).

NMR (DMSO-$d_6$, 400 MHz): δ=0.86(3H, t), 1.27(3H, m), 1.34(3H, m), 1.57 (2H, t), 1.64(2H, d), 2.00(1H, m), 2.27 (2H, t), 2.85(2H, t), 4.31(2H, d), 4.48(2H, d), 7.18(1H 1), 7.33(5H, m), 7.62(1H s), 9.24(1H, s), 12.42(1H, s).

EXAMPLE 6

1-(4-Benzylamino-5-ethylsulfonamidopurimidin-2-yl)-4-piperidinecarboxylic Acid

The title compound is obtained according to the procedure of Example 3 by using the compound prepared by Reference Example 14 and ethanesulfonyl chloride as starting materials. m.p. 205° C.

NMR(DMSO-$d_6$, 400 MHz): δ=1.22(3H, t), 1.33(2H, m), 1.75(2H, m), 2.45(1H, m), 2.88(2H, t), 3.04(2H, q), 4.40 (2H, d), 4.49(2H, d), 7.21(1H, t), 7.30(5H, m), 7.66(1H, s), 8.54(1H, s), 12.22(1H, s).

EXAMPLE 7

1-(4-Benzylamino-5-tridfluoromelhylsulfonamidopyrimidin-2-yl)-4-piperidine-carboxylic Acid 350 mg of the compound prepared by Reference Example 14 is dissolved in 40 ml of dichlormethane, and the solution is cooled to −70° C. under nitrogen atmosphere. 0.27 ml of triethylamine and 0.20 ml of trifluoromethanesulfonic anhydride are added to the solution and stirred for 1.5 hour at −70° C. The reaction solution is warmed to room temperature and washed with 30 ml of 1.5 N sodium hydroxide. The organic layer is dried over anhydrous magnesium sulfate and concentrated under reduced pressure to obtain the oily product. Column chromatography over silica gel (methanol dichloromethane=7.5% v/v) affords 280 mg of ester compound.

250 mg of the ester compound is dissolved in 30 ml of ethanol. 15 ml of 1.5 N sodium hydroxide is added to the solution, and stirred under reflux for 3.5 hours. The reaction solution is concentrated under reduced pressure to remove the organic solvent. The aqueous layer is adjusted to pH 3.5 by using 3.0 N hydrochloric acid and is stirred for 1 hour at 5° C. Filtration affords 160 mg of the title compound as a white solid. m.p. 160° C.

NMR (DMSO $d_6$, 400 MHz): δ=1.37(2H, m), 1.78(2H, m), 2.43(1H, m), 2.90(2H, t), 4.42(2H, d), 4.48(2H, d), 7.24(1H, t), 7.38(5H, m), 7.70(1H, s), 9.21(1H, s), 12.40 (1H, brs).

EXAMPLE 8

4-Benzylamino-5-(2-bromophenlylsulfonamido)-2-(4-ethylpiperazino)pyrimidine Hydrochloride 120 mg of the pre-base of the title compound is prepared by using the compound obtained by the Reference Example 15 and 2-bromobenzenesulfonyl chloride as starting materials according to the procedure of Example 3 and is dissolved in 15 ml of methanol. 4 ml of 5% HCl-methanol is added to the solution and stirred for 30 minutes at room temperature. The reaction solution is concentrated under reduced pressure to remove the solvent. Crystallization with diethyl ether and petroleum ether affords 95 mg of the title trihydrochloride compound. m.p. 67–70° C.

NMR (DMSO-$d_6$, 400 MHz): δ=1.18(3H, t), 2.50(6H, m), 3.79(4H, m), 4.69(2H, d), 6.12(1H, t), 7.30(5H, m), 7.40 (1H, s), 7.49(214, q), 7.82(1H, q), 8.80(1H, q).

EXAMPLE 9

4-Benzylamino-5-(4-chlorophenylsulfonamido)-2-(4-ethylpiperazino)-pyrimidine Hydrochloride 230 mg of the pre-base of the title compound is obtained by using the compound prepared by the Reference Example 15 and 4-chlorobenzenesulfonyl chloride as starting materials according to the procedure of Example 3 and is dissolved in 25 ml of methanol. 7 ml of 5% HCl-Methanol is added to the solution and stirred for 30 minutes at room temperature. The reaction solution is concentrated under reduced pressure to remove the solvent. Crystallization with diethyl ether and petroleum ether afforded 180 mg of the title trihydrochloride compound. m.p. 78–81° C.

NMR (DMSO-$d_6$, 400 MHz): δ=0.98(3H, t), 2.28(6H, m), 3.38(4H, m), 4.43(2H, d), 6.59(1H, t), 7.23(5H, m), 7.33 (2H, q), 7.36(1H, s), 7.61(2H, q).

EXAMPLE 10

5- (4-Chlorophenylsulfonamido)-4-(4-bromobenzylamino)-2-(1H-imidazol-1-yl)pyrimidine 150 mg of 4-chlorobenzenesulfonyl chloride is added to a solution of 220 mg of the compound prepared by the Reference Example 16 in 40 ml of dichloromethane at room temperature and stirred for 10 minutes. 0.13 ml of pyridine is added to the reaction solution, stirred for 30 minutes at room temperature and washed with 40 ml of 1.5 N sodium hydroxide. The organic layer is washed with 1H hydrochloric acid to remove the impure substance. The organic layer is dried over anhydrous magnesium sulfate and concentrated under reduced pressure to obtain thin yellow oily product. Crystallization with diethyl ether and petroleum ether affords 186 mg of the title compound. m.p. 183–185° C.

NMR (DMSO $d_6$, 400 MHz): δ=4.72(2H, d), 7.40(2H, d), 7.53(2H, d), 7.59(1H, s), 7.66(2H, d), 7.76(2H, d), 7.78(1H, t), 8.13(1H, t), 8.19(1H, d), 8.24(1H, d), 9.24(1H, s).

EXAMPLE 11

Ethyl 1-[5-(2-bromophenylsulfonamido)-4-(1,3-dioxaindan-5-yl)methylaminopyrimidin-2-yl)]4-piperidinecarboxylate 180 mg of 2-bromobenzenesulfonyl chloride is added to a solution of 310 mg of the compound prepared by the Reference Example 17 in 50 ml of ethanol at room temperature and stirred for 10 minutes. The yellowish reaction solution is further stirred for 55 hours at room temperature and concentrated under reduced pressure to remove the solvent. The oily product obtained therefrom is mixed with 70 ml of chloroform and washed with saturated sodium carbonate (100 ml×2). The organic layer is dried over anhydrous magnesium sulfate and is concentrated under reduced pressure to obtain oily product. Column chromatography on silica gel (ethyl acetate:hexane=1:1) afforded 290 mg of the title compound as a solid. m.p. 160–161° C.

NNM($CDCl_3$, 400 MHz): δ=1.17(3H, t), 1.57(2H, m), 1.80(2H, ABq), 2.41(1K m), 2.85(2H, m), 4.05(2H, q), 4.40(2H, t), 4.44(2H, d), 5.88(2H, s), 5.90(1H, t), 6.71(3H, m), 7.15(1H, s), 7.35(2K m), 7.68(1H, m), 7.83(1H, m).

EXAMPLE 12

1-[5-(4-Chloropenylsulfonamido)-4-(1,3-dioxaindan-5-yl)methylaminopyrimidin-2-yl)]-4-piperidinecarboxylic Acid 140 mg of 4-chlorobenzenesulfonyl chloride is added to a solution of 260 mg of the compound prepared by the Reference Example 17 in 40 ml of dichloromethane at room temperature and stirred for 10 minutes. 0.15 ml of pyridine is added to the reaction solution, and stirred for 45 hours at room temperature and washed with 30 ml of 1.5 N sodium hydroxide. The organic layer is dried over anhydrous magnesium sulfate and concentrated under reduced pressure to obtain 250 mg of the ester compound as a yellow solid.

250 mg of the ester compound is dissolved in 30 ml of ethanol. 15 ml of 1.5 N sodium hydroxide is added to the solution and stirred for 30 minutes at room temperature. The reaction solution is concentrated under reduced pressure to remove the organic layer. The aqueous layer is adjusted to pH 4.5 by using 3.0 N hydrochloric acid and stirred for 1 hour at SIC. Filtration affords 85 mg of the title compound as a white solid. m.p. 209–210° C.

NMR(DMSO-$d_6$, 400 MHz): δ=1.49(2H, m), 1.89(2H, m), 2.69(1H, m), 3.14(2H, m), 4.19(2H, brs), 4.41(2H, d), 6.00(2H, s), 6.72(1H, d), 6.83(1H, d), 6.85 (1H, d), 6.97(1H, s), 7.67(2H, m), 7.83(2H, m), 8.90(1H, brs), 9.96(1H, brs).

EXAMPLE 13

5-(2-Chloropenylcarboxamido)-4-(1,3-dioxaindan-5-yl)methylamino-2-(1H-2-ethyl-4-methylimidazol-1-yl)pyrimidine The title compound is obtained according to the procedure of Example 10 by using the compound prepared by Reference Example 18 and 2-chlorobenzoyl chloride as starting materials. m.p.: 152–154° C.

NMR DMSO-$d_6$, 400 MHz): δ=1.24(3H, t), 2.30(3H, d), 3.27(2H, q), 4.60(2H, d), 5.97(2H, s), 6.87(2H, d), 6.99(1H, s), 7.54(3H, M), 7.82(1H, q), 7.92(1H, d), 8.33(8.50(1H, t), 10.29(1H, s).

EXAMPLE 14

5-(2,4-Dinitrophenylcarboxamido)-4-(1,3-dioxaindan-5-yl)methylamino-2-(1H-2-ethyl-4-methylimidazol-1-yl)pyrimidine The title compound is obtained according to the procedure of Example 10 by using the compound prepared by Reference Example 18 and 2,4-dinitrobenzoyl chloride as starting materials. m.p.: 170–171° C.

NMR (DMSO-$d_6$, 400 MHz): δ=1.27(3H, t), 2.32(3H, d), 3.34(2H, q), 4.60(2H, d), 5.98(2H, d), 6.90(2H, d), 6.98(1H, s), 8.32(1H, s), 8.45(1H, t), 8.52(1H, s), 9.22(2H, d), 10.27 (1H, s) 10.66(1H, s).

EXAMPLE 15

Ethyl 1-[5-(4-bromophenylsulfonamido)-4-(1,3-dioxaindan-5-yl)methylaminopyrimidin-2-yl)]-4-piperazinecarboxylate 180 mg of 4-bromobenzenesulfonyl chloride is added to a solution of 250 mg of the compound prepared by the Reference Example 19 in 40 ml of dichloromethane at room temperature and stirred for 10 minutes. 0.15 ml of pyridine is added to the yellow reaction solution, and stirred for 30 hours at room temperature and washed with 50 ml of 1.5 N sodium hydroxide. The organic layer is dried over anhydrous magnesium sulfate and concentrated under reduced pressure to obtain oily product. The residue is purified by column chromatography on silica gel (methanol:dichloromethane=7.5% v/v). Crystallization with diethyl ether and petroleum ether afforded 165 mg of the title compound. m.p. 173–176° C.

NMR (CDCl$_3$, 400 MHz): δ=1.52(3H, t), 3.73(4H, d), 3.96(4H, d), 4.40(2H, q), 4.75(2H, d), 6.18(1H, t), 6.21(2H, s), 7.02(2H, d), 7.06(1H, s), 7.51(1H, s), 7.89(4H, m), 8.05(1H, t), 8.45(1H, t), 9.11(1H, s).

EXAMPLE 16

5-(4-Chlorophenylsulfonamido)-4-(1,3-dioxaindan-5-yl)methylamino-2-(1H-imidazol-1-yl)pyrimidine 140 mg of 4-chlorobenzenesulfonyl chloride is added to a solution of 210 mg of the compound prepared by the Reference Example 20 in 60 ml of dichloromethane at room temperature and stirred for 10 minutes. 0.15 ml of pyridine is added to the reaction solution, and stirred for 24 hours at room temperature and washed with 40 ml of 1.5 N sodium hydroxide. The organic layer is washed with 1N hydrochloric acid to remove the impure material. The organic layer is dried over anhydrous magnesium sulfate and concentrated under reduced pressure to obtain thin yellow oily product. Crystallization with diethyl ether and petroleum ether afforded 130 mg of the title compound. m.p. 206–207° C.

NMR (DMSO-d$_6$, 400 MHz): δ=4.45(2H, d), 5.97(2H, s), 6.76(1H, d), 6.83(1H, d), 6.89(1H, t), 7.05(1H, s), 7.47(1H, s), 7.65(2H, d), 7.74(2H, d), 7.76(1H, s), 7.97(1H, t), 8.40 (1H, s), 9.69(1H, s).

EXAMPLE 17

5-Ethylsulfoneamido-4-(1,3-dioxaindan-5-yl)methylamino-2-(1H-imidazol-1-yl)pyrimidine The title compound is obtained according to the procedure of Example 16 by using the compound prepared by Reference Example 20 and ethane-sulfonyl chloride as starting materials. m.p.: 188–190° C. NMR(DMSO-d$_6$, 400 MHz): δ=1.24(3H, t), 3.18(2H, q), 4.57(2H, d), 5.97(2H, s), 6.86 (1H, d), 6.94(1H, d), 7.02(1H, d), 7.08(1H, q), 7.82(1H, t), 8.03(1H, s), 8.05(1H, t), 8.45(1H, t), 9.11(1H, brs).

EXAMPLE 18

5-Hexylcarboxamido-4-(1,3-dioxaindan-5-yl)methylamino2-(1H-imidazol-1-yl)pyrimidine The title compound is obtained according to the procedure of Example 16 by using the compound prepared by Reference Example 20 and hexanoyl chloride as starting materials. m.p. 148–150° C.

NMR(DMSO d$_6$, 400 MHz): δ=0.90(313, t), 1.14(4H, m), 1.60(2H, m), 2.35(2H, t), 4.56(2H, d), 5.96(2H, s), 6.86(1H, d), 6.91(1H, d), 7.03(1H, d), 7.07(1H, s), 7.81(1H, s), 7.83(1H, t), 8.09(1H d), 8.32(1H, s), 9.22(1H, s).

EXAMPLE 19

4-Benzylamino-5-(4-bromophenylsulfonamido)-2-(1H-tetrazol-1-yl)pyrimidine 310 mg of 4-bromobenzenesulfonyl chloride is added to a solution of 270 mg of the compound prepared by the Reference Example 21 in 100 ml of acetonitrile at room temperature, and stirred for 10 minutes. 0.24 ml of pyridine is added to the solution, stirred for 40 hours at room temperature and concentrated under reduced pressure to remove acetonitrile. The residue is suspended in 30 ml of methanol, washed with 40 ml of 1.5 N sodium hydroxide, and filtered to obtain 186 mg of the title compound as a white solid. m.p. 184° C.

NMR (DMSO-d$_6$, 400 MHz): δ=4.58(2H, d), 7.31(5H, m), 7.71(2H, d), 7.76(1H, s), 7.78(2H, d), 8.38(1H, t), 9.97(1H, s), 10.06(1H, s).

EXAMPLE 20

4-Benzylamino-5-(2,4-dinitrophenylcarboxamido)-2-(1H-tetrazol-1-yl)-pyrimidine 310 mg of dinitrobenzoyl chloride is added to a solution of 270 mg of the compound prepared by the Reference Example 21 in 100 ml of acetonitrile at room temperature and stirred for 10 minutes. 0.24 ml of pyridine is added to the solution, stirred for 40 hours at room temperature, and concentrated under reduced pressure to remove acetonitrile. The residue is suspended in 30 ml of methanol, washed with 40 ml. of 1.5 N sodium hydroxide, and extracted with 50 ml of dichloromethane. The organic layer is washed with 50 ml of 1N hydrochloric acid to remove the impure material. The organic layer is dried over anhydrous magnesium sulfate and concentrated under reduced pressure to obtain 186 mg of the title compound as a white solid. m.p. 235° C. (decomposition).

NMR (DMSO-d$_6$, 400 MHz): δ=4.77(2H, d), 7.23(1H, t), 7.33(2H, t), 7.45(2H, d), 8.32(1H, s), 8.58(1H, t), 9.05(1H, s), 9.20(2H, d), 10.11(1H, s), 10.69(1H, s).

EXAMPLE 21

4-Benzylamino-5-(hexylcarboxamido)-2-(1H-tetrazol-1-yl)pyrimidine 310 mg of hexanoyl chloride is added to a solution of 270 mg of the compound prepared by the Reference Example 21 in 100 ml of acetonitrile at room temperature and stirred for 10 minutes. 0.24 ml of pyridine is added to the solution, stirred for 40 hours at room temperature, and concentrated under reduced pressure to remove acetonitrile. The residue is suspended in 30 ml of methanol, washed with 40 ml of 1.5 N sodium hydroxide, and extracted with 50 ml of dichlormethane. The organic layer is washed with 50 ml of 1N hydrochloric acid to remove the impure material. The organic layer is dried over anhydrous magnesium sulfate and concentrated under reduced pressure to obtain 186 mg of the title compound as a white solid. m.p. 144–145° C.

NMR (DMSO-d$_6$, 400 MHz): δ=0.89(3H, t), 1,31(4H, m), 1,59(2H, t), 2.38(2H, t), 4.46(2H, d), 7.25(1H, t), 7.33(2H, t), 7.45(2H, d), 8.10(1H, d), 8.34(1H, s), 9.35(1H, s), 10.06 (1H, s).

It will be understood that various changes and modifications can be made in the details of procedure, formulation and use without departing from the spirit of the invention, especially as defined in the following claims.

We claim:

1. A method of treating a mammal having precancerous lesions comprising administering a pharmacologically effective amount of a compound of Formula I or pharmaceutically acceptable salt thereof:

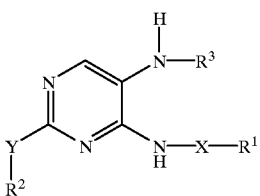

wherein
- X is selected from the group consisting of a direct bond, $C_{1-4}$ alkylene, $C_{1-4}$ alkyleneoxy, $C_{1-4}$ alkoxyphenyl or phenyl $C_{1-4}$ alkylene;
- Y is selected from the group consisting of a direct bond or $C_{1-2}$ alkyl;
- $R^1$ is selected from the group consisting of (i) 5–15 membered cyclic or branched chain heterocompound which includes one or two selected from a group consisting of nitrogen, oxygen and sulfur and which is substituted with one or two selected from a group consisting of hydrogen, halogen, nitro, hydroxy, $C_{1-6}$ alkyl, $C_{3-6}$ alkenyl and halogen $C_{1-4}$ alkoxy, (ii) $C_{4-10}$ carbocyclic compound or (iii) hydroxy $C_{1-4}$ alkoxy;
- $R^2$ is selected from the group consisting of 5–15 membered cyclic or branched chain heterocompound which includes one or two selected from a group consisting of nitrogen, oxygen and sulfur and which is substituted with one or two selected from a group consisting of hydrogen, hydroxy, halogen, nitro, hydroxy $C_{1-5}$ alkyl, $C_{1-6}$ alkyl, $C_{3-6}$ alkenyl, and halogen $C_{1-4}$ alkoxy;
- $R^3$ is selected from the group consisting of hydrogen, —C(O)$R^4$, or —S(O)$_2R^5$;
- $R^4$ and $R^5$ are each independently selected from the group consisting of hydroxy, $C_{1-6}$ alkyl, $C_{3-7}$ cycloalkyl, $C_{3-6}$ alkenyl, halogen, $C_{1-6}$ alkyl, halogen, $C_{2-6}$ alkenyl and $C_{1-4}$ alkoxy; or $R_4$ and $R_5$ represent each independently

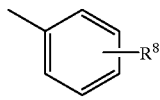

and $R_6$ is selected from a group consisting of hydrogen, hydroxy, $C_{1-6}$ alkyl, $C_{3-6}$ alkenyl, halogen, $C_{1-6}$ alkyl, halogen, nitro and $C_{1-4}$ alkoxy.

2. The method according to claim 1 wherein the compound is selected from a group consisting of
- 1-[4-benzylamino-5-(2-bromophenylsulfonamido) pyrimidin-2-yl]-4-piperidine-carboxylic acid;
- 1-[4-benzylamino-5-(4-bromophenylsulfonamido) pyrimidin-2-yl]-4-piperidine-carboxylic acid;
- 1-[4-benzylamino-5-(4-methylphenylsulfonamido) pyrimidin-2-yl]-4-piperidine-carboxylic acid;
- 1-[4-benzylamino-5-(2-chlorophenylsulfonamido) pyrimidin-2-yl]-4-piperidine-carboxylic acid;
- 1-(4-benzylamino-5-hexylcarboxamidopyrimidin-2-yl)-4-piperidinecarboxylic acid;
- 1-(4-benzylamino-5-ethylsulfonamidopyrimidin-2-yl)-4-piperidinecarboxylic acid;
- 1-[4-benzylamino-5-trifluoromethylsulfonamidopyrimidin-2-yl)-4-piperidine-carboxylic acid;
- ethyl 1-[5-(2-bromophenylsulfonamido)-4-(1,3-dioxaindan-5-yl)methylamino-pyrimidin-2-yl]-4-piperidinecarboxylate;
- 1-[5-(4-chlorophenylsulfonamido)-4-(1,3-dioxaindan-5-yl)methylaminopyrimidin-2-yl]-4-piperidinecarboxylic acid;
- 5-(4-chlorophenylsulfonamido)-4-(1,3-dioxaindan-5-yl) methylamino-2-(1H-imidazol-1-yl)pyrimidine;
- 5-ethylsulfonamido-4-(1,3-dioxaindan-5-yl)methylamino-2-(1H-imidazol-1-yl)-pyrimidine;
- 5-hexylcarboxamido-4-(1,3-dioxaindan-5-yl)methylamino-2-(1H-imidazol-1-yl)-pyrimidine;
- ethyl 1-[5-(4-bromophenylsulfonamido)-4-(1,3-dioxaindan-5-yl)methylamino-pyrimidin-2-yl]-4-piperazinecarboxylate;
- 5-(4-chlorophenylsulfonamido)-4N-(4-bromobenzylamino)-2-(1H-imidazol-1-yl)-pyrimidine;
- 5-(2-chlorophenylcarboxamido)-4-(1,3-dioxaindan-5-yl) methylamino-2-(1H-2-ethyl-4-methylimidazol-1-yl) pyrimidine;
- 5-(2,4-dinitrophenylcarboxamido)-4-(1,3-dioxaindan-5-yl)methylamino-2-(1H-2-ethyl-4-methylimidazol-1-yl) pyrimidine;
- 4-benzylamino-5-(2-bromophenylsulfonamido)-2-(1H-tetrazol-1-yl)pyrimidine;
- 4-benzylamino-5-(2,4-dinitrophenylcarboxamido)-2-(1H-tetrazol-1-yl)pyrimidine;
- 4-benzylamino-5-(2-hexylcarboxamido)-2-(1H-tetrazol-1-yl)pyrimidine;
- 4-benzylamino-5-(2-bromophenylsulfonamido)-2-(4-ethylpiperazino)pyrimidine; or
- 4-benzylamino-5-(4-chlorophenylsulfonamido)-2-(4-ethylpiperazino)pyrimidine.

3. A method for inhibiting the growth of neoplastic cells comprising exposing the cells to a growth inhibiting effective amount of a compound of Formula I or pharmaceutically acceptable salt thereof

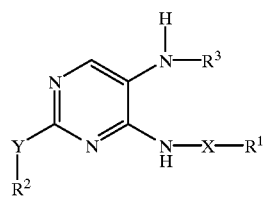

wherein
- X is selected from the group consisting of a direct bond, $C_{1-4}$ alkylene, $C_{1-4}$ alkyleneoxy, $C_{1-4}$ alkoxyphenyl or phenyl $C_{1-4}$ alkylene;
- Y is selected from the group consisting of a direct bond or $C_{1-2}$ alkyl;
- $R^1$ is selected from the group consisting of (i) 5–15 membered cyclic or branched chain heterocompound which includes one or two selected from a group consisting of nitrogen, oxygen and sulfur and which is substituted with one or two selected from a group consisting of hydrogen, halogen, nitro, hydroxy, $C_{1-6}$ alkyl, $C_{3-6}$ alkenyl and halogen $C_{1-4}$ alkoxy, (ii) $C_{4-10}$ carbocyclic compound or (iii) hydroxy $C_{1-4}$ alkoxy;
- $R^2$ is selected from the group consisting of 5–15 membered cyclic or branched chain heterocompound which includes one or two selected from a group consisting of nitrogen, oxygen and sulfur and which is substituted with one or two selected from a group consisting of hydrogen, hydroxy, halogen, nitro, hydroxy $C_{1-5}$ alkyl, $C_{1-6}$ alkyl, $C_{3-6}$ alkenyl, and halogen $C_{1-4}$ alkoxy;

R³ is selected from the group consisting of hydrogen, —C(O)R⁴, or —S(O)₂R⁵;

R⁴ and R⁵ are each independently selected from the group consisting of hydroxy, $C_{1-6}$ alkyl, $C_{3-7}$ cycloalkyl, $C_{3-6}$ alkenyl, halogen $C_{1-6}$ alkyl, halogen, $C_{2-6}$ alkenyl and $C_{1-4}$ alkoxy; or $R_4$ and $R_5$ represent each independently

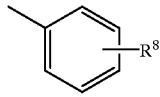

and $R_6$ is selected from a group consisting of hydrogen, hydroxy, $C_{1-6}$ alkyl, $C_{3-6}$ alkenyl, halogen, $C_{1-6}$ alkyl, halogen, nitro and $C_{1-4}$ alkoxy.

4. The method according to claim 3 wherein the compound is selected from a group consisting of 1-[4-benzylamino-5-(2-bromophenylsulfonamido)pyrimidin-2-yl]-4-piperidine-carboxylic acid;

1-[4-benzylamino-5-(4-bromophenylsulfonamido)pryimidin-2-yl]-4-piperidine-carboxylic acid;

1-[4-benzylamino-5-(4-methylphenylsulfonamido)pyrimidin-2-yl]-4-piperidine-carboxylic acid;

1-[4-benzylamino-5-(2-chlorophenylsulfonamido)pyrimidin-2-yl]-4-piperidine-carboxylic acid;

1-(4-benzylamino-5-hexylcarboxamidopyrimidin-2-yl)-4-piperidinecarboxylic acid;

1-(4-benzylamino-5-ethylsulfonamidopyrimidin-2-yl)-4-piperidinecarboxylic acid;

1-[4-benzylamino-5-trifluoromethylsulfonamidopyrimidin-2-yl)-4-piperidine-carboxylic acid;

ethyl 1-[5-(2-bromophenylsulfonamido)-4-(1,3-dioxaindan-5-yl)methylamino-pyrimidin-2-yl]-4-piperidinecarboxylate;

1-[5-(4-chlorophenylsulfonamido)-4-(1,3-dioxaindan-5-yl)methylaminopyrimidin-2-yl]-4-piperidinecarboxylic acid;

5-(4-chlorophenylsulfonamido)-4-(1,3-dioxaindan-5-yl)methylamino-2-(1H-imidazol-1-yl)pyrimidine;

5-ethylsulfonamido-4-(1,3-dioxaindan-5-yl)methylamino-2-(1H-imidazol-1-yl)-pyrimidine;

5-hexylcarboxamido-4-(1,3-dioxaindan-5-yl)methylamino-2-(1H-imidazol-1-yl)-pyrimidine;

ethyl 1-[5-(4-bromophenylsulfonamido)-4-(1,3-dioxaindan-5-yl)methylamino-pyrimidin-2-yl]-4-piperazinecarboxylate;

5-(4-chlorophenylsulfonamido)-4N-(4-bromobenzylamino)-2-(1H-imidazol-1-yl)-pyrimidine;

5-(2-chlorophenylcarboxamido)-4-(1,3-dioxaindan-5-yl)methylamino-2-(1H-2-ethyl-4-methylimidazol-1-yl)pyrimidine;

5-(2,4-dinitrophenylcarboxamido)-4-(1,3-dioxaindan-5-yl)methylamino-2-(1H-2-ethyl-4-methylimidazol-1-yl)pyrimidine;

4-benzylamino-5-(2-bromophenylsulfonamido)-2-(1H-tetrazol-1-yl)pyrimidine;

4-benzylamino-5-(2,4-dinitrophenylcarboxamido)-2-(1H-tetrazol-1-yl)pyrimidine;

4-benzylamino-5-(2-hexylcarboxamido)-2-(1H-tetrazol-1-yl)pyrimidine;

4-benzylamino-5-(2-bromorophenylsulfonamido)-2-(4-ethylpiperazino)pyrimidine; or 4-benzylamino-5-(4-chlorophenylsulfonamido)-2-(4-ethylpiperazino)pyrimidine.

5. A method for regulating apoptosis in human cells comprising exposing said cells to an effective amount of a compound of the formula:

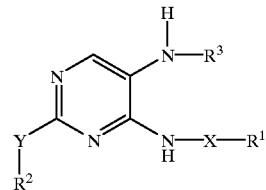

wherein

X is selected from the group consisting of a direct bond, $C_{1-4}$ alkylene, $C_{1-4}$ alkyleneoxy, $C_{1-4}$ alkoxyphenyl or phenyl $C_{1-4}$ alkylene;

Y is selected from the group consisting of a direct bond or $C_{1-2}$ alkyl;

R¹ is selected from the group consisting of (i) 5–15 membered cyclic or branched chain heterocompound which includes one or two selected from a group consisting of nitrogen, oxygen and sulfur and which is substituted with one or two selected from a group consisting of hydrogen, halogen, nitro, hydroxy, $C_{1-6}$ alkyl, $C_{3-6}$ alkenyl and halogen $C_{1-4}$ alkoxy, (ii) $C_{4-10}$ carbocyclic compound or (iii) hydroxy $C_{1-4}$ alkoxy;

R² is selected from the group consisting of 5–15 membered cyclic or branched chain heterocompound which includes one or two selected from a group consisting of nitrogen, oxygen and sulfur and which is substituted with one or two selected from a group consisting of hydrogen, hydroxy, halogen, nitro, hydroxy $C_{1-5}$ alkyl, $C_{1-6}$ alkyl, $C_{3-6}$ alkenyl, and halogen $C_{1-4}$ alkoxy;

R³ is selected from the group consisting of hydrogen, —C(O)R⁴, or —S(O)₂R⁵;

R⁴ and R⁵ are each independently selected from the group consisting of hydroxy, $C_{1-6}$ alkyl, $C_{3-7}$ cycloalkyl, $C_{3-6}$ alkenyl, halogen $C_{1-6}$alkyl, halogen, $C_{2-6}$ alkenyl and $C_{1-4}$ alkoxy; R⁴ and R⁵ represent each independently

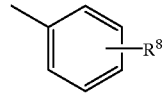

and $R_6$ is selected from a group consisting of hydrogen, hydroxy, $C_{1-6}$ alkyl, $C_{3-6}$ alkenyl, halogen, $C_{1-6}$ alkyl, halogen, nitro and $C_{1-4}$ alkoxy.

6. The method according to claim 5 wherein the compound is selected from a group consisting of 1-[4-benzylamino-5-(2-bromophenylsulfonamido)pyrimidin-2-yl]-4-piperidine-carboxylic acid;

1-[4-benzylamino-5-(4-bromophenylsulfonamido)pryimidin-2-yl]-4-piperidine-carboxylic acid;

1-[4-benzylamino-5-(4-methylhenylsulfonamido)pyrimidin-2-yl]-4-piperidine-carboxylic acid;

1-[4-benzylamino-5-(2-chlorophenylsulfonamido)pyrimidin-2-yl]-4-piperidine-carboxylic acid;

1-(4-benzylamino-5-hexylcarboxamidopyrimidin-2-yl)-4-piperidinecarboxylic acid;

1-(4-benzylamino-5-ethylsulfonamidopyrimidin-2-yl)-4-piperidinecarboxylic acid;

1-[4-benzylamino-5-trifluoromethylsulfonamidopyrimidin-2-yl]-4-piperidine-carboxylic acid;

ethyl 1-[5-(2-bromophenylsulfonamido)-4-(1,3-dioxaindan-5-yl)methylamino-pyrimidin-2-yl]-4-piperidinecarboxylate;

1-[5-(4-chlorophenylsulfonamido)-4-(1,3-dioxaindan-5-yl)methylaminopyrimidin-2-yl]-4-piperidinecarboxylic acid;

5-(4-chlorophenylsulfonamido)-4-(1,3-dioxaindan-5-yl)methylamino-2-(1H-imidazol-1-yl)pyrimidine;

5-ethylsulfonamido-4-(1,3-dioxaindan-5-yl)methylamino-2-(1H-imidazol-1-yl)-pyrimidine;

5-hexylcarboxamido-4-(1,3-dioxaindan-5-yl)methylamino-2-(1H-imidazol-1-yl)-pyrimidine;

ethyl 1-[5-(4-bromophenylsulfonamido)-4-(1,3-dioxaindan-5-yl)methylamino-pyrimidin-2-yl]-4-piperazinecarboxylate;

5-(4-chlorophenylsulfonamido)-4N-(4-bromobenzylamino)-2-(1H-imidazol-1-yl)-pyrimidine;

5-(2-chlorophenylcarboxamido)-4-(1,3-dioxaindan-5-yl)methylamino-2-(1H-2-ethyl-4-methylimidazol-1-yl)pyrimidine, 5-(2,4-dinitrophenylcarboxamido)-4-(1,3-dioxaindan-5-yl)methylamino-2-(1H-2-ethyl-4-methylimidazol-1-yl)pyrimidine;

4-benzylamino-5-(2-bromophenylsulfonamido)-2-(1H-tetrazol-1-yl)pyrimidine;

4-benzylamino-5-(2,4-dinitrophenylcarboxamido)-2-(1H-tetrazol-1-yl)pyrimidine;

4-benzylamino-5-(2-hexylcarboxamido)-2-(1H-tetrazol-1-yl)pyrimidine;

4-benzylamino-5-(2-bromophenylsulfonamido)-2-(4-ethylpiperazino)pyrimidine; or 4-benzylamino-5-(4-chlorophenylsulfonamido)-2-(4-ethylpiperazino)pyrimidine.

\* \* \* \* \*